US011638708B2

(12) United States Patent
Breder

(10) Patent No.: US 11,638,708 B2
(45) Date of Patent: May 2, 2023

(54) METHOD OF TREATMENT OF AGGRESSION

(71) Applicant: Supernus Pharmaceuticals, Inc., Rockville, MD (US)

(72) Inventor: Christopher D. Breder, Bethesda, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 16/240,389

(22) Filed: Jan. 4, 2019

(65) Prior Publication Data

US 2020/0022986 A1 Jan. 23, 2020

Related U.S. Application Data

(63) Continuation of application No. 16/046,858, filed on Jul. 26, 2018, now Pat. No. 10,201,547, which is a continuation of application No. 15/782,334, filed on Oct. 12, 2017, now Pat. No. 10,058,556, which is a continuation of application No. 13/951,642, filed on Jul. 26, 2013, now Pat. No. 9,801,887, which is a continuation of application No. 12/654,455, filed on Dec. 18, 2009, now abandoned.

(60) Provisional application No. 61/193,735, filed on Dec. 19, 2008.

(51) Int. Cl.
*A61K 31/5377* (2006.01)
*A61K 31/00* (2006.01)

(52) U.S. Cl.
CPC .......... *A61K 31/5377* (2013.01); *A61K 31/00* (2013.01)

(58) Field of Classification Search
CPC combination set(s) only.
See application file for complete search history.

(56) References Cited

U.S. PATENT DOCUMENTS

| 4,148,896 | A | 4/1979 | Smith, Jr. et al. |
| 5,202,128 | A | 4/1993 | Morella et al. |
| 6,344,215 | B1 | 2/2002 | Bettman et al. |
| 6,613,763 | B2 | 9/2003 | Comings et al. |
| 7,737,133 | B2 | 6/2010 | Devane et al. |
| 7,761,144 | B2 | 7/2010 | Cox et al. |
| 8,129,360 | B2 | 3/2012 | Jaeger et al. |
| 8,748,472 | B2 | 6/2014 | Chang et al. |
| 2002/0028761 | A1 | 3/2002 | Koppel et al. |
| 2002/0156078 | A1 | 10/2002 | Comings et al. |
| 2004/0170684 | A1 | 9/2004 | Anand et al. |
| 2004/0180088 | A1 | 9/2004 | Dudhara et al. |
| 2005/0004105 | A1 | 1/2005 | Leahy et al. |
| 2006/0078609 | A1 | 4/2006 | Vandecruys et al. |
| 2006/0147527 | A1 | 7/2006 | Bachmann et al. |
| 2007/0219201 | A1 | 9/2007 | Carroll, Jr. et al. |
| 2008/0038346 | A1 | 2/2008 | Eisenreich et al. |
| 2008/0069878 | A1 | 3/2008 | Venkatesh et al. |
| 2009/0004229 | A1 | 1/2009 | Pastini et al. |
| 2009/0220611 | A1 | 9/2009 | Dargelas et al. |
| 2010/0173907 | A1 | 7/2010 | Breder |
| 2011/0144042 | A1 | 6/2011 | Duchaussoy et al. |
| 2011/0244042 | A1 | 10/2011 | Chang et al. |
| 2014/0050797 | A1 | 2/2014 | Venkatesh et al. |
| 2014/0013526 | A1 | 5/2014 | Hamm |
| 2014/0135326 | A1 | 5/2014 | Hamm |
| 2015/0086629 | A1 | 3/2015 | Chang et al. |

FOREIGN PATENT DOCUMENTS

| EP | 1 354 585 A1 | 10/2003 |
| GB | 2447949 A | 10/2008 |
| JP | S54-143526 A | 11/1979 |
| JP | 2003-113086 A | 4/2003 |
| JP | 2007-529829 A | 10/2007 |
| JP | 2008-500325 A | 1/2008 |
| JP | 2008-189616 A | 8/2008 |
| JP | 2009-510036 A | 3/2009 |
| JP | 2010-502645 A | 1/2010 |
| WO | WO 2004/106298 A1 | 12/2004 |
| WO | WO 2005/121113 A1 | 12/2005 |
| WO | WO 2006/070781 A1 | 7/2006 |
| WO | WO-2010/080603 A2 | 7/2010 |

OTHER PUBLICATIONS

Gadow (Oppositional Defiant Disorder as a Clinical Phenotype in Children with Autism Spectrum Disorder, J Autism Dev Disord. Aug. 2008 ; 38(7): 1302-1310, renumbered pp. 1-11).*
Yoshioka, "Effect of Moisture on Stability of Solid Dosage Forms," Pharm Tech Japan, 1990, vol. 6, No. 8, pp. 891-905.
Bagnall et al,. "Molindone for schizophremia and severe mental illness (Review)," Cochrane Database Syst. Rev., 2007(1):CD002083, 62 pages.
Findling et al., "Effectiveness, Safety, and Pharmacokinetics of Quetiapine in Aggressive Children with Conduct Disorder," J. Am. Acad. Child Adolesc. Psychiatry, Jul. 2006, 45(7):792-800.
Findling, Robert L., M.D., "Treatment of Aggression in Children," Primary Care Companion J. Clin. Psychiatry, 2003, 5(Supp6):5-9.
Greenhill et al., "Molindone Hydrochloride in the Treatment of Aggressive, Hospitalized Children," Psychopharmacol. Bull., Jan. 1981, 17(1):125-127.
Greenhill et al., "Molindone Hydrochloride Treatment of Hospitalized Children with Conduct Disorder," J. Clin. Psychiatry, Aug. 1985, 46(8:Sec.2):20-25.
Hartman et al., "Molecular Attributes of Dopamine Receptors: New Potential for Antipsychotic Drug Development," Ann. Med., 1996, 28:211-219.
Holmes et al., "Behavioral Characterization of Dopamine D5 Receptor Null Mutant Mice," Behavioral Neuroscience, 2001, 115(5):1129-1144.

(Continued)

Primary Examiner — Kathrien A Hartsfield
(74) Attorney, Agent, or Firm — Foley & Lardner LLP

(57) ABSTRACT

The invention comprises a method of treatment of aggression and similar behavioral syndromes, such as impulsivity and irritability, by a pharmaceutical agent exhibiting combined D2 and D5 antagonistic activity.

5 Claims, 5 Drawing Sheets

(56) References Cited

OTHER PUBLICATIONS

Itil et al., "Treatment of Human Aggression with Major Tranquilizers, Antidepressants, and Newer Psychotropic Drugs," The Journal of Nervous and Mental Disease, 1975, 160(2):83-99.

Jensen et al., "Consensus Report on Impulsive Aggression as a Symptom Across Diagnostic Categories in Child Psychiatry: Implications for Medication Studies," J. Am. Acad. Child Adolesc. Psychiatry, Mar. 2007, 46(3):309-321.

Maher et al. "Dopamine system genes and attention deficit hyperactivity disorder: a meta-analysis," Psychiatric Genetics, 2002, 12(4):207-215.

Matsumoto et al,. "Neurons in the Thalamic CM-Pf Complex Supply Striatal Neurons with Information About Behaviorally Significant Sensory Events," J. Neurophysiol., 2001, 85(2):960-976.

McClellan et al., "Treatment of Early-Onset Schizophremia Spectrum Disorders (TEOSS): Rationale, Design, and Methods," J. Am. Acad. Child Adolesc. Psychiatry, Aug. 2007, 46(8):969-978.

Sikich et al., "Double-Blind Comparison of First- and Second-Generation Antipsychotics in Early-Onset Schizophrenia and Schizoaffective Disorder: Findings From the Treatment of Early-Onset Schizophremia Spectrum Disorders (TEOSS) Study," Am. J. Psychiatry, Nov. 2008, 165(11):1420-1431.

Vanyukov et al., "Antisociality, Substance Dependence, and the DRD5 Gene: A Preliminary Study," American Journal of Medical Genetics (Neuropsychiatric Genetics), 2000, 96(5):654-658.

Bassarath et al., "Medication Strategies in Childhood Aggression: A Review," Can. J. Psychiatry, Jul. 2003, 48(6):367-373.

Jordan et al., "The Antipsychotic Aripiprazole is a Potent, Partial Agonist at the Human 5-HT1A Receptor," European Journal of Pharmacology, 2002, 441:137-140.

Claustre et al., SSR181507, A Dopamine D2 Receptor Antagonist and 5-HT1A Receptor Agonist. I: Neurochemical and Electrophysiological Profile, 2003, Neuropsychopharmacology, 2003, 28:2064-2076.

Yoshioka, Sumie, "Effect of Moisture on Stability of Solid Dosage Forms," Pharm. Tech. Japan, 1990, 6(8):891-905.

Malone et al., "Aggression Classification and Treatment Response," Psychopharmacology Bulletin, 1998, 34(1):41-45.

Andersen et al., "Comparison of the pharmacological characteristics of [3H]raclopride and [3H]SCH 23390 binding to dopamine receptors in vivo in mouse brain", European Journal of Pharmacology, 1988, vol. 146, pp. 113-120.

De Coninck et al., "The use of flupenthixol ('Fluanxol') in the management of behavioural disorders in disturbed and psychotic children", Pharmatherapeutica, 1982, vol. 3, No. 3, pp. 209-214.

Frye et al., "Clozapine in bipolar disorder: treatment implications for other atypical antipsychotics", Journal of Affective Disorders, 1998, vol. 48, pp. 91-104.

Hoefgen et al., "Dopamine/Serotonin receptor ligands. 10:1 SAR studies on Azecine-type Dopamine Receptor ligands by functional screening at human cloned D1, D2L, and D5 receptors with a microplate reader based calcium assay lead to a novel potent D1/D5 selective antagonist", Journal of Medicinal Chemistry, 2006, vol. 49, pp. 760-769.

Jasovic-Gasic et al., "Efficacy of clozapine therapy in aggression", European Psychiatry, Editions Scientifiques et Medicales Elsevier, 1998, vol. 13, p. 314s.

Monkhouse, "Stability aspects of preformulation and formulation of solid pharmaceuticals", Drug Development and Industrial Pharmacy, 1984, vol. 10, pp. 1373-1412.

Nikulina et al., "Strain differences in clonidine-induced aggressiveness in mice and its interaction with the dopamine system", Pharmacology Biochemistry and Behavior, 1993, vol. 44, pp. 821-825.

Shima, "Technology of Controlled Release", Japan, 2003, pp. 11-20, and 112-121.

Shioji, "Manufacture Technology of Solid Tablets", Japan, 2003, pp. 15-32, 39-46, 73, and 84-88.

Supplementary European Search Report issued in co-pending European Patent Application No. 09 83 7980, dated May 9, 2016.

Office Action issued in counterpart Japanese Patent Application No. 2013-502785 dated Dec. 15, 2015.

Wetzel et al., "Amisulpride versus flupentixol in schizophrenia with predominantly positive symptomology—a double-blind controlled study comparing a selective D2-like antagonist to a mixed D1-/D2-like antagonist", Psychopharmacology, Jun. 1998, vol. 137, No. 3, pp. 223-232.

English translation of Office Action issued in co-pending Japanese Application No. 2015-542030, dated Mar. 28, 2017.

Office Action issued in co-pending Japanese Application No. 2015-204851, dated Sep. 13, 2016.

Stocks et al., "A phase 2a randomized, parallel group, dose-ranging study of molindone in children with Attention-Deficit/Hyperactivity Disorder and persistent, serious conduct problems", Journal of Child and Adolescent Psychopharmacology, 2012, vol. 22, No. 2, pp. 102-111.

Extended European Search Report issued in co-pending European Patent Application No. 17180576.5, dated Dec. 20, 2017.

Dudzinski et al. "Preformulation Studies I: Molindone Hydrochloride"; Journal of Pharmaceutical Sciences; vol. 62, Issue 4; pp. 622-624; (Apr. 1973).

Office Action dated Jul. 27, 2020 in MX/a/2019/001413.

Posey et al., "Antipsychotics in the treatment of autism," Journal of Clinical Investigation, Jan. 2, 2008, 118(1):6-14.

\* cited by examiner

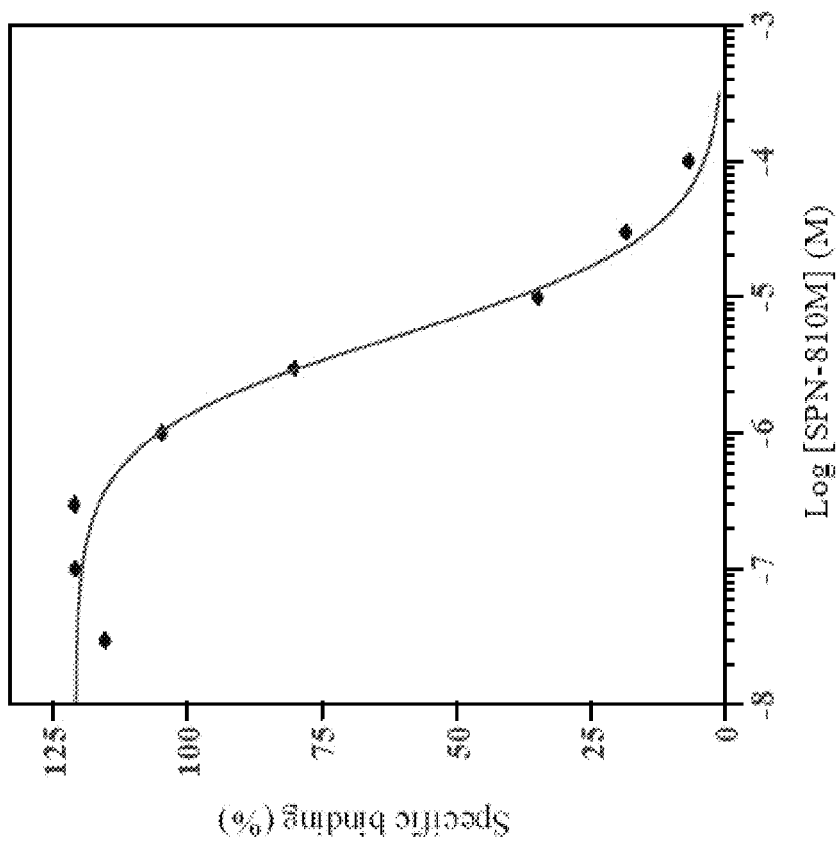
Figure 1: Competition curve obtained with compound SPN-810M at the human D5 receptor

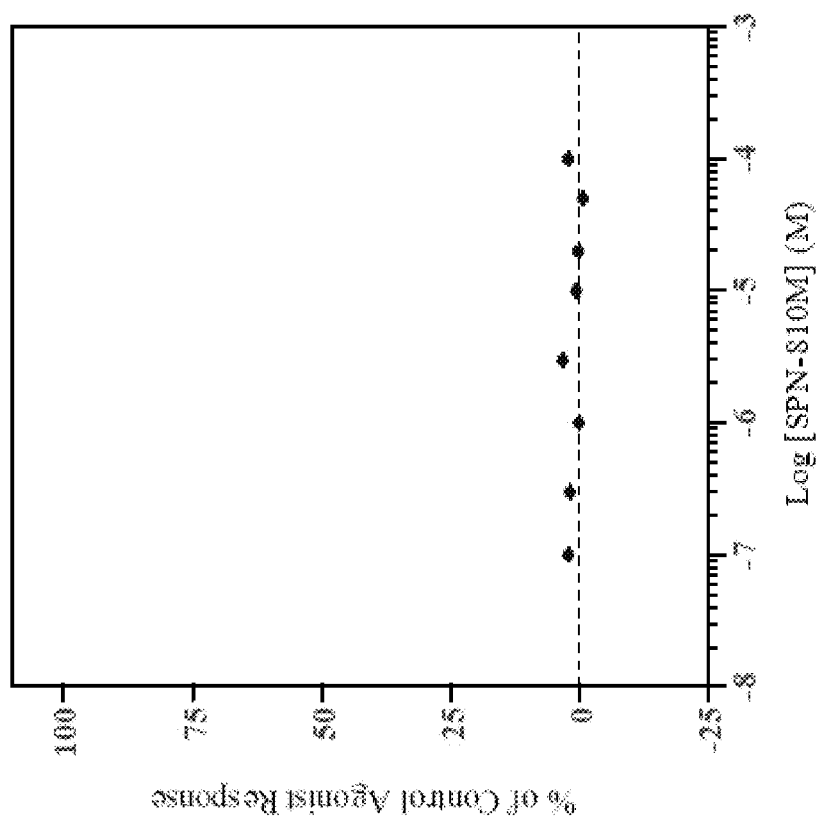
Figure 2: Agonist Effect of Compound SPN-810M at the Human D5 Receptor

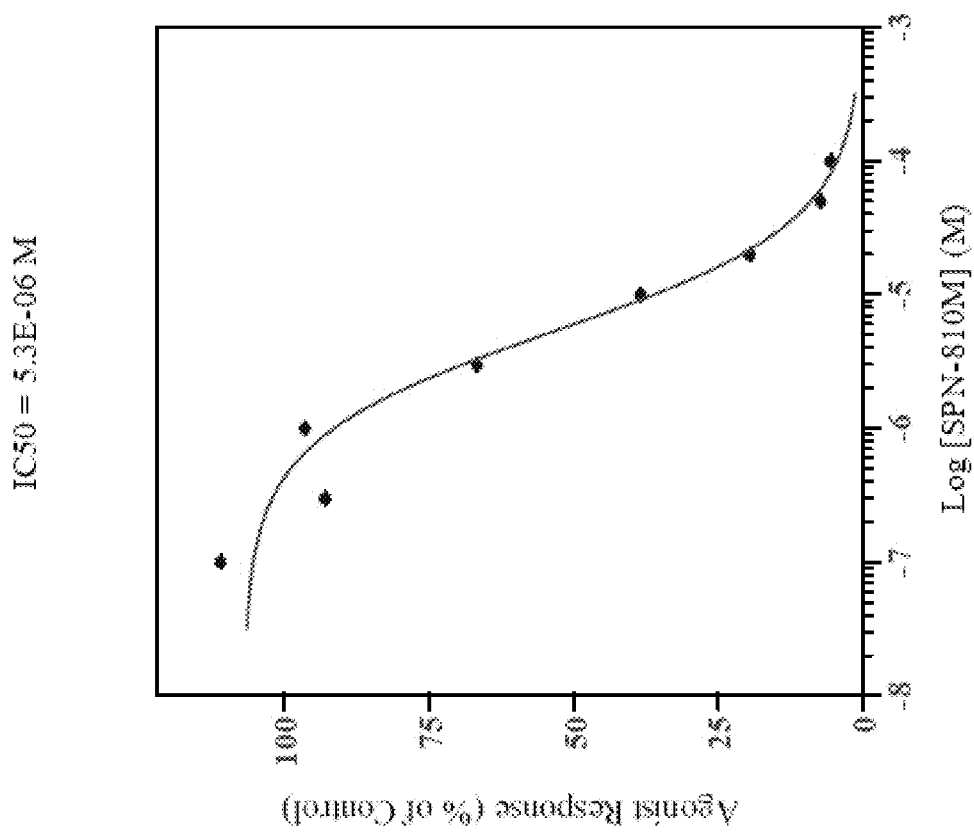
Figure 3: Antagonist Effect of Compound SPN-810M at the Human D5 receptor

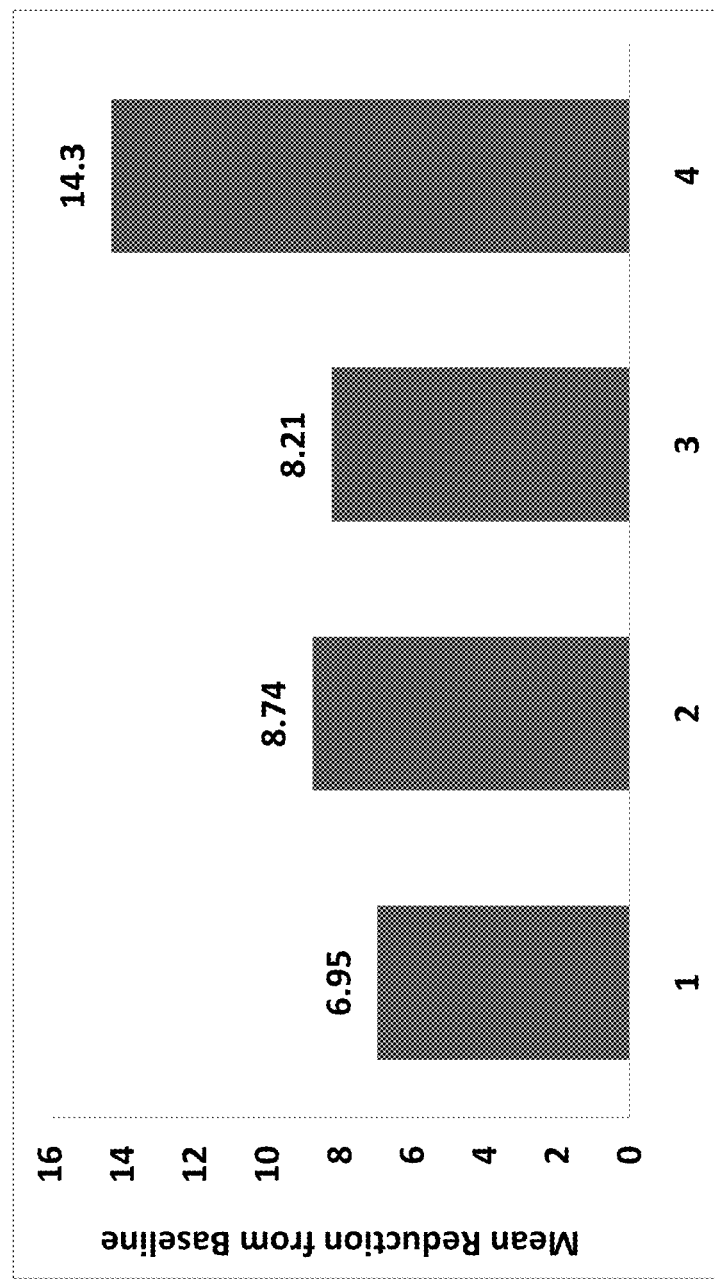

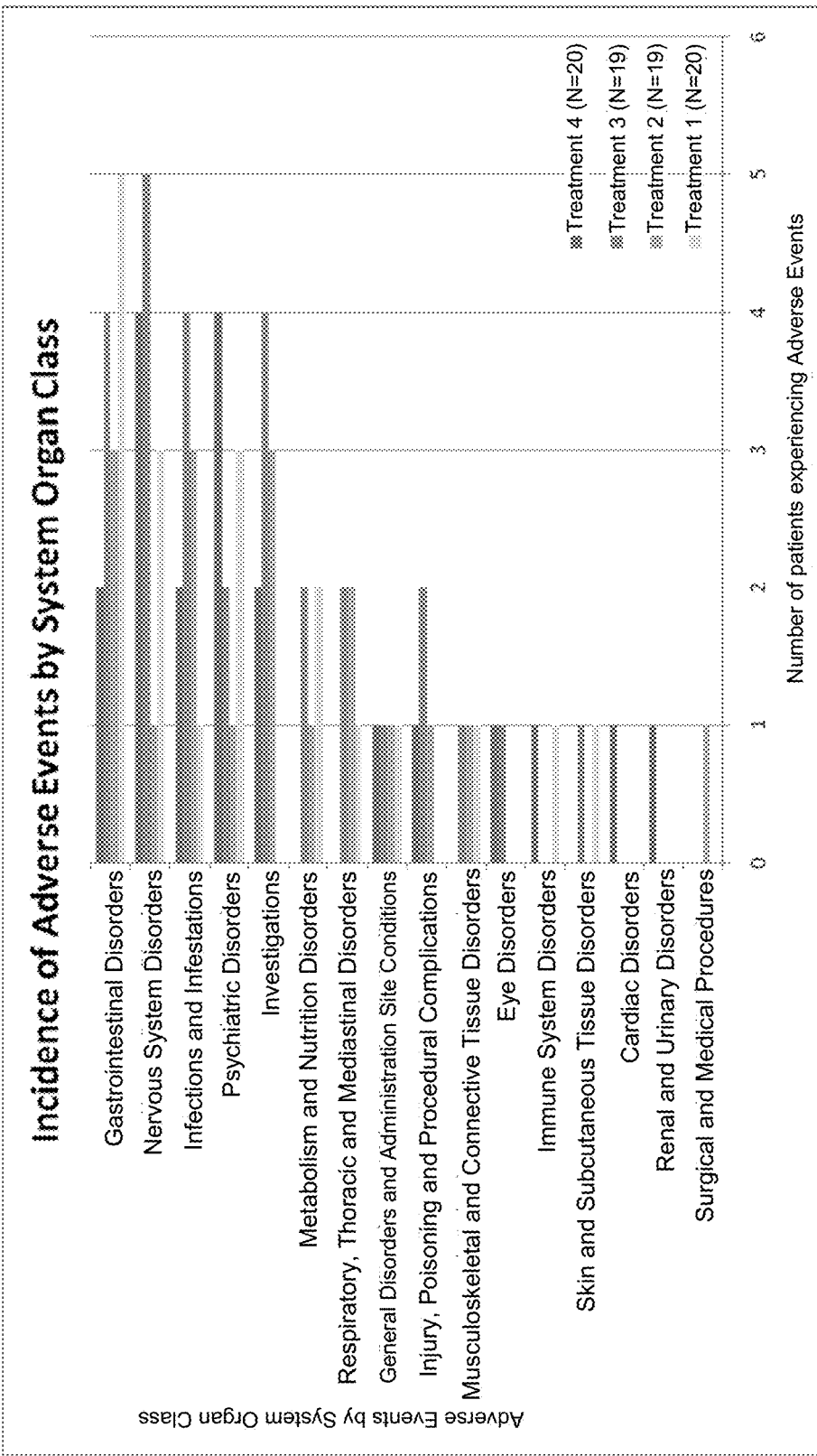
Fig. 5  Incidences of Adverse Events

METHOD OF TREATMENT OF AGGRESSION

CROSS-REFERENCE TO RELATED APPLICATIONS

This application is a Continuation of U.S. application Ser. No. 16/046,858, filed Jul. 26, 2018, which is a Continuation of U.S. application Ser. No. 15/782,334, filed Oct. 12, 2017, which is a Continuation of U.S. patent application Ser. No. 13/951,642, filed Jul. 26, 2013, which is a Continuation of U.S. application Ser. No. 12/654,455, filed Dec. 18, 2009, which claims priority from U.S. Provisional Application No. 61/193,735, filed Dec. 19, 2008, the entire contents of which are incorporated herein by reference.

BACKGROUND

Aggression and similar syndromes, including impulsivity and irritability, represent a broad category of behaviors that complicate the management of several disease states, such as attention deficit hyperactivity disorder (ADHD), bipolar disorder, autism, and post traumatic stress disorder. In some cases, 25-50% of patients optimally treated for the underlying disorder continue to manifest these syndromes (J Am Acad Child Adolesc Psychiatry. 2007 March; 46(3):309-22.).

Dopaminergic therapies are among the most prescribed for these behavioral syndromes, and include such molecules as haloperidol and other antipsychotics. The dopamine receptors for these molecules are grouped into 2 families: the D1, which includes the D1 and D5 receptor, and the D2, which includes the D2, D3 and D4 receptors. The two families differ by the manner in which the receptor protein is incorporated into the cell membrane, and by the pharmacology of the molecules that have an affinity for each type. Each receptor type is a distinct entity with its unique gene, anatomy in the brain and affinity for different molecules. Some dopamine receptor subtypes, such as the D2 receptor, have further modifications in the protein structure, giving rise to further subclassification, e.g., $D2^{short}$ and $D2_{long}$.

There is increasing evidence that D5 receptor activity would be beneficial in the treatment of aggression and similar behavioral syndromes.

The D5 receptor has very specific localization in the brain, and is found in such areas as the Parafascicular Nucleus of the Thalamus, as well as the prefrontal cortex, hippocampus, ventral tegmental area, Substantia Nigra and Raphe nucleus (Hartman D S, Civelli O. Molecular attributes of dopamine receptors: new potential for antipsychotic drug development. Ann Med 1996; 28(3):211-9). The Parafascicular nucleus is involved in the behavioral process of attention to critical sensory input and activation of the subject toward that stimulus. One of the important paradigms in which the Parafascicular nucleus participates is the activation of the fight or flight response. Therefore, the Parafascicular nucleus is likely involved in activating early components of aggressive behavior (Matsumoto N, Minamimoto T, Graybiel A M, Kimura M. Neurons in the thalamic CM-Pf complex supply striatal neurons with information about behaviorally significant sensory events. J Neurophysiol 2001; 85(2):960-76).

The gene for the D5, DRD5, is associated with impulsiveness and with symptomology associated with disruptive behavioral disorders, such as antisocial personality disorder (Vanyukov M M, Moss H B, Kaplan B B, Kirillova G P, Tarter R E. Antisociality, substance dependence, and the DRD5 gene: a preliminary study. Am J Med Genet 2000; 96(5):654-8). DRD5 is also associated with genetic transmission of a number of disorders associated with aggression, irritability and impulsivity, including schizophrenia, Tourette's and ADHD (Maher B S, Marazita M L, Ferrell R E, Vanyukov M M. Dopamine system genes and attention deficit hyperactivity disorder: a meta-analysis. Psychiatr Genet 2002; 12(4):207-15). Blockade of the D5 receptor in a knockout model is associated with decreased motor activity, which may be akin to decreased aggression (Holmes A, Hollon T R, Gleason T C, et al. Behavioral characterization of dopamine D5 receptor null mutant mice. Behav Neurosci 2001; 115(5):1129-44).

Molindone is a typical antipsychotic drug that has high affinity for D2 family of dopamine receptors. where it is thought to exert its therapeutic action. Molindone was previously suggested for the treatment of aggression in both adult and pediatric patients (Greenhill L L, Barmack J E, Spalten D, Anderson M, Halpern F. Molindone Hydrochloride in the treatment of aggressive, hospitalized children [proceedings]. Psychopharmacol Bull 1981; 17(1):125-7; Itil T M, Wadud A. Treatment of human aggression with major tranquilizers, antidepressants, and newer psychotropic drugs. J Nerv Ment Dis 1975; 160(2-1):83-99). Molindone was also evaluated for children with the early-onset schizophrenia spectrum disorders (J Am Acad Child Adolesc Psychiatry, 2007, August, 46:8, p. 969-978 and Am J Psychiatry, 165:11, November 2008).

For adults with schizophrenia, the dose of molindone may range from 100 to 225 mg per day (Bagnall A, Fenton M, Kleijnen J, Lewis R. Molindone for schizophrenia and severe mental illness. Cochrane Database Syst Rev 2007 (1): CD002083). In general, the dose of other antipsychotics used for the treatment of aggressive behavior are about 50% relative to those used for the treatment of psychosis in schizophrenia (J Am Acad Child Adolesc Psychiatry. 2006 July; 45(7):792-800).

SUMMARY OF THE INVENTION

The current invention offers a method of treatment of aggression and/or similar behavioral syndromes, including irritability and impulsivity that comprises the steps of: 1. selecting several active agents with known activity (e.g., agonist or antagonist) on at least one dopaminergic, serotonergic or gabaergic receptor where the opposite activity is associated with aggressive behavior; 2. conducting a receptor screening assay on these same receptor families with each of the active agents to identify activity for at least one additional receptor having a known association with undesired (i.e., aggressive) behavior; 3. determining if said activity is agonistic or antagonistic in nature; 4. by the results of steps 2 and 3, choosing among the screened active agents at least one that targets the most diverse types of aggression-associated receptors; 5. optimizing the total dose of the active agent(s), taking into account results of steps 2 through 4; and 6. administering the dose of step (5) to a mammalian subject.

In one embodiment of the invention, the mammalian subject is a human child. In another embodiment of the invention, the mammalian subject is an adult human.

Identification of agonist/antagonist activity in the active agents that exhibit the potential as therapeutics for aggression and similar behavioral syndromes is important, since it allows for selection of drugs that have more than one therapeutic target (e.g., both D2 and D5 receptors). This is superior to taking a combination of therapies to achieve multiple targets because of the enhanced patient compliance with the reduced pill load. It also can lead to a lower dose, since different receptor activities may be additive, or even synergistic, in their effect.

Use of molecules that target a specific class of receptors with a limited distribution in the brain is also potentially beneficial in that it limits the potential for side effects. This restricted set of neural pathways is less likely to have "off-target" effect in the systems not involved in the desired activity.

In one embodiment, the invention comprises a method of treatment of aggression and similar behavioral syndromes, such as impulsivity and irritability in a mammalian subject, by a pharmaceutical agent exhibiting combined D2 and D5 antagonistic activity.

In another embodiment, the invention discloses a method of treatment of aggression and similar behavioral syndromes by a pharmaceutical agent exhibiting combined D2 and D5 antagonistic activity, wherein the total dosage of the pharmaceutical agent is smaller than the dosage anticipated on the premise of D2 activity only.

In yet another embodiment of the invention, the pharmaceutical agent is molindone.

BRIEF DESCRIPTION OF THE DRAWINGS

FIG. 1 shows a competition curve obtained with compound SPN-810M (molindone) at the human D5 receptor.

FIG. 2 shows the agonist effect of compound SPN-810M at the Human D5 Receptor.

FIG. 3 shows the antagonist effect of compound SPN-810M at the Human D5 receptor.

FIG. 4 shows a reduction in Conduct Problem Subscale Score achieved through administration of molindone in a randomized, multicenter, parallel group dose-ranging study in children with ADHD and persistent serious conduct problems.

FIG. 5 shows an adverse effect profile of molindone in a randomized, multicenter, parallel group dose-ranging study in children with ADHD and persistent serious conduct problems

DETAILED DESCRIPTION OF THE PREFERRED EMBODIMENTS

It was unexpectedly discovered that, in addition to the well-documented D2-receptor group antagonistic activity, molindone has specific antagonist activity at the D5 dopaminergic receptor.

A heterologous competition assay was designed for a receptor affinity screening of molindone. Recombinant D5 receptors were expressed in a GH4 cell line and specific binding was characterized by displacement of another molecule with affinity for the D5 receptor (the "ligand"). "Specific binding" refers here to the difference in the binding of the ligand to the receptors in the presence and absence of an excess of the active agent. An initial screen was performed with $10^{-5}$ μM molindone. The conditions and results of the assay are summarized in the Tables 1 and 2.

TABLE 1

Conditions of the displacement assay for molindone

| Assay | Ligand | Conc. | Non-specific | Incubation | Method of detection |
|---|---|---|---|---|---|
| $D_1$ (h) | [$^3$H]SCH 23390 | 0.3 nM | SCH 23390* (1 μM) | 60 min./22° C. | Scintillation counting |
| $D_{2S}$ (h) | [$^3$H]spiperone | 0.3 nM | (+)butaclamol (10 μM) | 60 min./22° C. | Scintillation counting |
| $D_3$ (h) | [$^3$H]spiperone | 0.3 nM | (+)butaclamol (10 μM) | 60 min./22° C. | Scintillation counting |
| $D_5$ (h) | [$^3$H]SCH 23390 | 0.3 nM | SCH 23390 (10 μM) | 60 min./22° C. | Scintillation counting |

*Sch 23390 is a highly potent and selective dopamine D1-like receptor antagonist with a K(i) of 0.2 and 0.3 nM for the D1 and D5 dopamine receptor subtypes, respectively.

TABLE 2

Results of the displacement assay for molindone (concentration 1.0E−05M)

| Assay | % Inhibition of control specific binding |
|---|---|
| D1 | 55 |
| D2s | 98 |
| D3 | 100 |
| D4.4 | 38 |
| D5 | 59 |

The affinity of molindone for the D5 receptor was further characterized by determining the IC50, or concentration that inhibits 50% of control specific binding. For this experiment, a range of molindone concentrations was selected for the ligand blocking assay. The IC50 was determined using non-linear regression analysis of the competition curves using Hill equation curve fitting. The inhibition constants Ki, wherein Ki is defined as the concentration of the competing ligand (molindone) that will bind to half the binding sites at equilibrium in the absence of radioligand or other competitors, were calculated using Cheng Prusoff equation. The results of the affinity assay are summarized in Tables 3 and 4, and in FIG. 1.

TABLE 3

IC$_{50}$ Determination: Individual Data

| Receptor | Test Concentration (M) | % of Control Specific Binding | | |
|---|---|---|---|---|
| | | 1st | 2nd | Mean |
| D$_1$ (h) | 3.0E−08 | 105.5 | 95.5 | 102.0 |
| | 1.0E−07 | 95.6 | 96.5 | 96.0 |
| | 3.0E−07 | 93.4 | 92.6 | 93.0 |
| | 1.0E−06 | 90.9 | 70.3 | 80.6 |
| | 3.0E−06 | 52.2 | 56.8 | 54.5 |
| | 1.0E−05 | 31.6 | 30.7 | 31.1 |
| | 3.0E−05 | 18.4 | 12.6 | 15.5 |
| | 1.0E−04 | 2.8 | 3.7 | 3.2 |
| D$_{2S}$ (h) | 3.0E−10 | 99.1 | 95.6 | 97.3 |
| | 3.0E−09 | 95.8 | 104.6 | 100.2 |
| | 1.0E−08 | 91.0 | 94.7 | 92.8 |
| | 3.0E−08 | 68.0 | 71.9 | 69.9 |
| | 1.0E−07 | 22.0 | 28.1 | 25.1 |
| | 3.0E−07 | 4.4 | 1.9 | 3.1 |
| | 1.0E−06 | 0.1 | −0.7 | −0.3 |
| | 1.0E−05 | −1.7 | −3.0 | −2.4 |
| D$_3$ (h) | 3.0E−10 | 98.4 | 100.0 | 99.2 |
| | 3.0E−09 | 103.7 | 102.6 | 103.2 |
| | 1.0E−08 | 101.9 | 107.3 | 104.6 |
| | 3.0E−08 | 99.3 | 90.6 | 94.9 |
| | 1.0E−07 | 71.4 | 63.4 | 67.4 |
| | 3.0E−07 | 31.4 | 32.3 | 31.9 |
| | 1.0E−06 | 8.1 | 9.1 | 8.6 |
| | 1.0E−05 | −1.0 | 0.9 | −0.1 |
| D$_5$ (h) | 3.0E−08 | | 123.6 | 115.3 |
| | 1.0E−07 | 106.9 | 130.3 | 120.8 |
| | 3.0E−07 | 111.2 | 132.3 | 120.9 |
| | 1.0E−06 | 109.6 | 118.9 | 104.7 |
| | 3.0E−06 | 90.5 | 78.1 | 80.2 |
| | 1.0E−05 | 82.2 | 43.4 | 34.9 |
| | 3.0E−05 | 26.3 | 18.3 | 18.5 |
| | 1.0E−04 | 18.6 | 8.3 | 6.8 |

TABLE 4

IC50 Determination for Molindone: Summary Results

| Assay | Reference compound | IC$_{50}$ (M) | K$_1$ (M) | n$_{(H)}$ |
|---|---|---|---|---|
| D1 | SCH 23390 | 3.9E−06 | 1.5E−06 | 0.9 |
| D2s | (+)butaclamol | 5.1E−08 | 1.7E−08 | 1.7 |
| D3 | (+)butaclamol | 1.6E−07 | 3.6E−08 | 1.4 |
| D5 | SCH 23390 | 5.2E−06 | 2.4E−06 | 1.2 |

The final step of the assay was to characterize whether the binding is of an agonist or antagonist nature. For the D5 receptor, this was accomplished through an assay that examined the agonist effect on the D5 receptor, i.e., the generation of cAMP or the blockade of this effect when stimulated by a D5 agonist, dopamine. This was also done with a range of concentrations to determine the relative agonist vs antagonist binding Ki. The EC$_{50}$ values (concentration producing a half-maximal specific response) and IC$_{50}$ values (a concentration causing a half-maximal inhibition of the control-specific agonist response) were determined by non-linear regression analysis of the concentration-response curves generated with mean replicate values using Hill equation curve fitting. The apparent dissociation constants for antagonists Kb were calculated using the modified Cheng Prusoff equation.

The conditions of the screening are presented in Table 5. It was found that molindone ($10^{-5}$ μM) exhibited 59% inhibition of the SCH23390 binding at the D5 receptor. The Ki was determined to be $2.4 \times 10^{-6}$. The binding was determined to be that of an antagonist. The full results of the screening are summarized in Tables 6-8 and in FIG. 2-3.

TABLE 5

Agonist/Antagonist screening Assay: Conditions

| Assay | Stimulus | Incubation | Reaction Product | Method of Detection |
|---|---|---|---|---|
| D$_1$ (h) (agonist effect) | None (10 μM dopamine for control) | 30 min./ 22° C. | cAMP | HTRF (Homogeneous Time Resolved Fluorescence) |
| D$_1$ (h) (antagonist effect) | Dopamine (1000 nM) | 30 min./ 22° C. | cAMP | HTRF |
| D$_{2S}$ (h) (agonist effect) | None (100 nM dopamine for control) | 20 min./ 37° C. | cAMP | HTRF |
| D$_{2s}$ (h) (antagonist effect) | Dopamine (30 nM dopamine for control) | 20 min./ 37° C. | cAMP | HTRF |
| D$_3$ (h) (agonist effect) | None (30 nM dopamine for control) | 10 min./ 37° C. | cAMP | HTRF |
| D$_3$ (h) (antagonist effect) | dopamine (10 nM) | 10 min./ 37° C. | cAMP | HTRF |
| D$_5$ (h) (agonist effect) | None (10 μM dopamine for control) | 30 min./ 22° C. | cAMP | HTRF |
| D5 (h) (antagonist effect) | Dopamine (100 nM) | 30 min./ 22° C. | cAMP | HTRF |

TABLE 6

IC$_{50}$ Determination for D$_5$ (h): Individual Data (Antagonist Effect)

| Test Concentration (M) | Agonist Response | | |
|---|---|---|---|
| | % of Control, 1$^{st}$ | % of Control, 2$^{nd}$ | % of Control, Mean |
| 1.0E−07 | 107 | 115 | 111.0 |
| 3.0E−07 | 90 | 95 | 92.9 |
| 1.0E−06 | 98 | 95 | 96.4 |
| 3.0E−06 | 67 | 66 | 66.7 |
| 1.0E−05 | 40 | 36 | 38.4 |
| 2.0E−05 | 19 | 20 | 19.6 |
| 5.0E−05 | 4 | 11 | 7.3 |
| 1.0E−04 | 7 | 4 | 5.6 |

TABLE 7

IC$_{50}$ Determination: Summary Results (Antagonist Effect)

| Receptor | IC$_{50}$ (M) | K$_B$ (M) |
|---|---|---|
| D$_1$ (h) | 3.1E−05 | 2.0E−06 |
| D$_{2S}$ (h) | 6.8E−08 | 4.7E−09 |
| D$_3$ (h) | 1.1E−06 | 7.1E−08 |
| D$_5$ (h) | 5.3E−06 | 9.2E−07 |

TABLE 8

EC$_{50}$ Determination for D$_5$ (h): Individual Data (Agonist Effect)

| Test Concentration (M) | Agonist Response | | |
|---|---|---|---|
| | % of Control, 1$^{st}$ | % of Control, 2$^{nd}$ | % of Control, Mean |
| 1.0E−07 | 2 | 2 | 2.1 |
| 3.0E−07 | 4 | −1 | 1.8 |
| 1.0E−06 | 0 | 0 | 0.1 |
| 3.0E−06 | 3 | 4 | 3.3 |
| 1.0E−05 | −1 | 2 | 0.6 |
| 2.0E−05 | −2 | 2 | 0.2 |
| 5.0E−05 | 1 | −2 | −0.7 |
| 1.0E−04 | 1 | 4 | 2.1 |

Based on the receptor findings, it was suggested that molindone may be effective for the treatment of aggression in humans, in particular, in children with ADHD, in smaller doses than is currently customary. A lower daily dose of the drug results in a diminishing frequency and severity of the adverse effects of the treatment to a level of tolerability, thus resulting in improvement in patient compliance.

In one embodiment, the invention is directed to a method of treatment of aggression in humans, in particular children, diagnosed with ADHD, bipolar disorder, autism, and post traumatic stress disorder by administering molindone in a total daily dose that is at least 10% lower than the current dose for its use as an antipsychotic agent. In other embodiments, the dose is 15% lower, 25% lower, 35% lower, and 50% lower than the current dose.

In one embodiment of the invention, molindone is administered in a dose range of from 10 mg/day to 200 mg/day. In other embodiments, molindone is administered in dose ranges of from 3 mg/day to 200 mg/day; 15 mg/day to 120 mg/day; 15 mg/day to 90 mg/day; 30 mg/day to 90 mg/day; or 36 mg/day to 72 mg/day.

The success of the treatment is evident in the marked decrease in the number instances of undesirable behavior exhibiting aggression, irritability and impulsivity. Such behavior may be exemplified, without limitation, by disobedience; negativism; provocative opposition to authority figures; violations of minor rules; temper tantrums; argumentativeness; provocative behavior; stubbornness; blaming others for his or her own mistakes; being touchy, easily annoyed, angry, resentful, spiteful or vindictive; and swearing.

In another embodiment, the invention encompasses a method of treatment of aggression in children with ADHD with molindone that is characterized by an improved adverse effect profile. The adverse effects that are diminished by the method of the present invention may be, but are not limited to, drowsiness, depression, hyperactivity and euphoria, extrapyramidal reactions, akathisia, akinesia, dystonic syndrome, tardive dyskinesia, tachycardia, nausea, dry mouth, urinary retention, and constipation.

The efficacy and the adverse effect profile of the lower dose treatment of the current invention were evaluated in a Randomized, Multicenter, Parallel Group, Dose Ranging Study to Evaluate the Safety and Tolerability of molindone in Children with Attention-Deficit-Hyperactivity Disorder (ADHD) and Persistent Serious Conduct Problems, where the subjects are administered molindone hydrochloride given 3 times daily in a dose range of 5 to 20 mg/day in children <30 kg, and 10 to 40 mg/day in children ≥30 kg (Example 1 and FIG. 4).

Example 1

Effectiveness, safety and tolerability of molindone was evaluated in a randomized, multicenter, parallel group dose-ranging study in children with ADHD and persistent serious conduct problems. Subjects were randomized based on weight at baseline to 1 of 4 treatment groups. The dosing for subjects with weight of less than 30 kg was initiated at 1.67 mg/day and 3.34 mg/day for subjects weighing 30 kg or more. A titration schedule was followed until the target dose (Treatment group 1, 2, 3 or 4) was reached. Subjects remained at target dose for 6 weeks (Table 9).

TABLE 9

Total daily dose by treatment group

| | Treatment group 1 | Treatment group 2 | Treatment group 3 | Treatment group 4 |
|---|---|---|---|---|
| <30 kg | 5 mg/day | 10 mg/day | 15 mg/day | 20 mg/day |
| ≥30 kg | 10 mg/day | 20 mg/day | 30 mg/day | 40 mg/day |

The study showed a statistically significant efficacy signal towards reducing Conduct Problem Subscale scores. (Table 10; FIG. 4).

TABLE 10

Mean Reduction from Baseline in NCBRF-TIQ: Conduct Problem Subscale Score

| | Treatment 1 | Treatment 2 | Treatment 3 | Treatment 4 |
|---|---|---|---|---|
| Baseline Mean | 20.35 | 25.74 | 26.00 | 25.95 |
| Visit 12 Mean | 13.40 | 17.00 | 17.79 | 11.65 |
| Mean Reduction | 6.95 | 8.74 | 8.21 | 14.30 |

Side effects from the administration of molindone in all four treatment groups were mild, self-limiting and within the limits of tolerability, i.e. no subjects discontinued the study because of the side effects (FIG. 5).

What is claimed is:

1. A method of treating a behavioral syndrome selected from impulsivity and irritability in a mammalian subject diagnosed with a single condition selected from the group consisting of bipolar disorder and post-traumatic stress disorder comprising administering to the subject a pharmaceutical agent exhibiting combined D2 and D5 antagonistic activity;

wherein the pharmaceutical agent is molindone.

2. The method of claim 1, wherein the behavioral syndrome is impulsivity.

3. The method of claim 1, wherein the behavioral syndrome is irritability.

4. The method of claim 1, wherein the agent is administered in a dose range of from 10 mg/day to 200 mg/day.

5. The method of claim 1, wherein said mammalian subject is a child.

* * * * *